United States Patent [19]

Holland

[11] 4,282,246

[45] Aug. 4, 1981

[54] ANTIDIABETIC FURANCARBOXYLIC AND THIPHENECARBOXYLIC ACIDS

[75] Inventor: Gerald F. Holland, Old Lyme, Conn.

[73] Assignee: Pfizer Inc., New York, N.Y.

[21] Appl. No.: 128,362

[22] Filed: Mar. 7, 1980

[51] Int. Cl.³ .................. A61K 31/38; A61K 31/34
[52] U.S. Cl. ................................ 424/275; 424/285
[58] Field of Search ............................ 424/285, 275

[56] References Cited

U.S. PATENT DOCUMENTS 4,011,333  3/1977  Parker ............................. 424/275

OTHER PUBLICATIONS

Chemical Abstracts, 69, 106542t; vol. 72 121350j; vol. 61, 16706h; vol. 81, 105148e; vol. 59, 14745e, (1963).
J. Med. Chem. 11, 984 (1968), Bauer et al.
J. Agr. Food Chem. 17, 931, (1969) Berteau et al.
Bull. Soc. Chem., Fr. 519, (1974) Bisagni et al.; 4115 (1967) Fournari et al.
Proc. Nat. Acad. Sci. U.S., 58, 2299 (1967)–Corredor.
J. Org. Chem., 41, 2835, (1976)—Divald et al.; 41, 2350, 1976–Ferraz et al.; vol. 42, 3717 (1977); 32, 2441 (1967).
Proc. Soc. Expt. Biol. Med. 118, 499 (1965); 121,777 (1966)—Dulin et al.
Metab. Clin. Exp. 18, 214 (1969)—Dulin et al.
J. Chem. Soc., 2551 1971—Elliott et al.; 66 (1944), Haworth et al.
Journal Am. Chem. Soc. 55, 2903 (1933); vol. 75, 3697 (1953).
Tetrahedron 23, 2443 (1967)–Gogte et al.
J. Heterocycl. Chem. 13, 1099 (1976)–Gronowitz et al.
Collection Czech. Chem. Communs, 41, 1541 (1976)—Janda et al.; 41 2571, (1976)—Kada et al.
J. Pharm. Sci. 57, 1014 (1968)—Lahiri et al.
Chem. Abstracts 54, 13094f (Lukes et al.) 1960; vol. 52, 6306e; vol. 52, 6306e (1958); vol. 58 5606g.
J. Org. Chem., vol. 21, 516 (1956).

Collection Czech. Chem. Commun. 39, 3527, (1974).
Chem. Abstracts 76, 153468c (1972); vol. 49, 13211b.
Bull. Soc. Chim. Belges 79, 575 (1970).
Chem. Abstracts, vol. 89, 109171v (1978).
Bull. Soc. Chim. Fr., 242 (1971).
Chem. Abstracts, vol. 59, 6341a.
J. Med. Chem. 8, 350 (1965).
Chem. Abstracts, vol. 27 2952.

Primary Examiner—Frederick E. Waddell
Attorney, Agent, or Firm—Connolly and Hutz

[57] ABSTRACT

Compounds of the structure

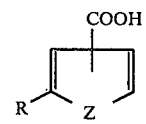

wherein
  Z is oxygen or sulfur;
  R is $(C_1-C_2)$alkoxy;
    phenoxy;
    benzyl;
    phenylthiomethyl;
    phenylthio;
    phenylthio monosubstituted in the 2-, 3- or 4-position with $(C_1-C_3)$alkyl, phenyl, methoxy, chloro, fluoro or trifluoromethyl;
    phenylthio disubstituted in the 2,5- or 3,5- positions with methyl, methoxy, chloro, or fluoro;
    2,3,5,6-tetrafluorophenylthio;
    1- or 2-naphthylthio;
    $(C_2-C_6)$alkylthio; or
    halo (bromo or chloro); and the pharmaceutically-acceptable salts thereof are useful in lowering the blood glucose levels of hyperglycemic mammals.

43 Claims, No Drawings

ANTIDIABETIC FURANCARBOXYLIC AND THIPHENECARBOXYLIC ACIDS

BACKGROUND OF THE INVENTION

In spite of the early discovery of insulin and its subsequent wide-spread use in the treatment of diabetes, and the later discovery and use of sulfonylureas (e.g. chlorpropamide, tolbutamide, acetohexamide, tolazamide) and biguanides (e.g. phenformin) as oral hypoglycemic agents, the treatment of diabetes remains less than satisfactory. The use of insulin, necessary in a high percentage of diabetics where available synthetic hypoglycemic agents are not effective, requires multiple daily, usually self, injection. Determination of the proper dosage of insulin requires frequent estimations of the sugar in the urine or in the blood. The administration of an excessive dose of insulin causes hypoglycemia, with effects ranging from mild abnormalities in blood glucose to coma, or even death. Where effective, synthetic hypoglycemic agents are preferred over insulin, being more convenient to administer and less prone to cause severe hypoglycemic reactions. However, the clinically available hypoglycemics are fraught with other toxic manifestations which limit their use. In any event, where one of these agents may fail in an individual case, another may succeed. The need for additional hypoglycemic agents, which may be less toxic or succeed where others fail, is clearly evident.

In addition to the hypoglycemic agents cited above, a variety of other compounds have been reported to possess this type of activity, including 5-methylpyrazole-3-carboxylic acid [Smith, et al., J. Med. Chem. 8, 350 (1965)], 3-methylisoxazole-5-carboxylic acid [Dulin and Gerritsen, Proc. Soc. Expt. Biol. Med. 121, 777 (1966)], 1-methyl-4-(5-methyl-3-pyrazolyl)pyridinium iodide [Dulin et al., Proc. Soc. Expt. Biol. Med. 118, 499 (1965)], 1-methyl-4-(3-methyl-5-isoxazolyl)pyridinium chloride [Bauer et al., J. Med. Chem. 11, 984 (1968)], 2-carboxypyrazine [Dulin and Gerritsen, Metab. Clin. Exp. 18, 214 (1969)], a series of hexahydroindeno(1,2-c)pyrroles and dialkylaminomethylindans [Lahiri and Pathak, J. Pharm. Sci. 57, 1013 (1968)], methylenecyclopropylacetic acid and 4-pentenoic acid [Corredor et al., Proc. Nat. Acad. Sci. U.S. 58, 2299 (1967)].

In many cases the compounds of the present invention are known from the literature:

5-Methoxyfuran-2-carboxylic acid [Manly and Amstutz, J. Org. Chem. 21, 516 (1956)];

5-Ethoxyfuran-2-carboxylic acid [Manly and Amstutz, loc. cit.];

5-Methoxythiophene-2-carboxylic acid [Sicé, J. Am. Chem. Soc. 75, 3697 (1953)];

5-Phenoxyfuran-2-carboxylic acid [Manly and Amstutz, loc. cit.];

5-Benzylfuran-2-carboxylic acid [Mndzhoyan et al., Doklady Akad. Nauk Armyan. S.S.R. 25, 133 (1957); Chem. Abstr. 52, 6306e; Tsukervanik and Galust'yan, Dokl. Akad. Nauk. Uz. S.S.R. 20, 26 (1963); Chem. Abstr. 59, 6341a; potential plant stimulant].

5-Benzylfuran-3-carboxylic acid [Fr. patent 1,578,377; insecticide];

5-Benzylthiophene-2-carboxylic acid [MacDowell and Patrick, J. Org. Chem. 32, 2441 (1967)];

3-Phenylthiomethylthiophene-2-carboxylic acid [Tagawa and Ueno, Chem. Pharm. Bull. 26, 1384 (1978); synthetic intermediate in synthesis of non-steroidal antiinflammatory agents];

5-Phenylthiofuran-2-carboxylic acid [Manly and Amstutz, loc. cit.; Kada et al., Collection Czech. Chem. Commun. 41, 2571 (1976)];

5-(4-Methylphenylthio)furan-2-carboxylic acid [Kada et al., loc. cit.];

5-(4-Methoxyphenylthio)furan-2-carboxylic acid [Kada et al., loc. cit.];

5-(4-Chlorophenylthio)furan-2-carboxylic acid [Kada, et al., loc. cit.];

5-Bromofuran-2-carboxylic acid [Whittaker, Rec. Trav. Chim. 52, 352 (1933); German Patent 1,172,938 (Chem. Abstr. 61, 16706h); food preservative];

5-Bromofuran-3-carboxylic acid [Gilman and Burtner, J. Am. Chem. Soc. 55, 2903 (1933)];

2-Bromofuran-3-carboxylic acid [Gilman and Burtner loc. cit.];

5-Bromothiophene-2-carboxylic acid [Fournari et al., Bull. Soc. Chim. Fr., 4115 (1967); Parker, U.S. Pat. No. 4,011,333; intermediate for hypolipidemic agents];

5-Bromothiophene-3-carboxylic acid [Fournari et al., loc. cit.];

2-Bromothiophene-3-carboxylic acid [Fournari et al., loc. cit.]; Gronowitz and Pettersson, J. Heterocycl. Chem 13, 1099 (1976);

5-Chlorofuran-2-carboxylic acid [Nazarova and Babaev, Zh. Obstrch. Khim. 32, 723 (1962); Chem. Abstr. 58, 5606g];

2-Chlorofuran-3-carboxylic acid [Roques et al., Bull. Soc. Chim. Fr., 242 (1971)];

5-Chlorothiophene-2-carboxylic acid [Gronowitz and Pettersson, loc. cit; Parker, loc. cit.; intermediate for hypolipidemic agents];

5-Chlorothiophene-3-carboxylic acid [Sone et al., Nippon Kagaku Zasshi 92, 1193 (1971); Chem. Abstr. 76, 153468c]; and 2-Chlorothiophene-3-carboxylic acid [Dafgard et al., Acta. Pharm. Suec. 11, 309 (1974); Chem. Abstr. 81, 105148e].

The pharmaceutical use of these compounds, in particular their use as hypoglycemic agents, however, is novel.

SUMMARY OF THE INVENTION

It has now been found that compound of the structure

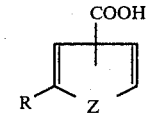

wherein
Z is oxygen or sulfur;
R is $(C_1-C_2)$alkoxy;
 phenoxy;
 benzyl;
 phenylthiomethyl;
 phenylthio;
 phenylthio monosubstituted in the 2-, 3- or 4-position with $(C_1-C_3)$alkyl, phenyl, methoxy, chloro, fluoro or trifluoromethyl;
 phenylthio disubstituted in the 2,5- or 3,5- positions with methyl, methoxy, chloro, or fluoro;
 2,3,5,6-tetrafluorophenylthio;
 1- or 2-naphthylthio;

($C_2$-$C_6$)alkylthio; or halo (bromo or chloro); and the pharmaceutically-acceptable cationic salts thereof, when administered to rodents in appropriate amount, either orally or parenterally, will lower the level of blood glucose, projecting clinical use of these compounds to reduce the blood levels of glucose in hyperglycemic mammals, including man, to acceptable values.

By the term "pharmaceutically-acceptable cationic salts" is intended salts such as the alkali metal salts, e.g., sodium and potassium; alkaline earth metal salts such as calcium and magnesium; aluminum salts; ammonium salts; and salts with organic bases, e.g., amines such as benzathine (N,N'-dibenzylethylenediamine), choline, diethanolamine, ethylenediamine, meglumine (N-methylglucamine), benethamine(N-benzylphenethylamine), diethylamine, piperazine, and tromethamine(2-amino-2-hydroxymethyl-1,3-propanediol).

Because they possess a particularly high level of activity, compounds of special value in this invention are 5-substituted furan-2-carboxylic acids wherein the substituent is phenylthio, phenylthiomethyl or methoxy; 5-substitutedthiophene-2-carboxylic acids wherein the substituent is phenylthio, 3-methylphenylthio, 3-chlorophenylthio or benzyl; and 5-substituted furan-3-carboxylic acids wherein the substituent is phenylthio, 3- or 4-methylphenylthio, 2-methoxyphenylthio, 2-, 3- or 4-chlorophenylthio, 2-, 3- or 4-fluorophenylthio, 2,5- or 3,5-difluorophenylthio, 1-naphthylthio or bromo.

Because they possess an exceptionally high level of activity, compounds of greatest value in this invention are 5-substituted furan-2-carboxylic acids wherein the substituent is phenylthiomethyl or methoxy and 5-substituted furan-3-carboxylic acids wherein the substituent is phenylthio, 3-chlorophenylthio, 2- or 3-fluorophenylthio, 2,5- or 3,5-difluorophenylthio or 2,3,5,6-tetrafluorophenylthio.

DETAILED DESCRIPTION OF THE INVENTION

The furancarboxylic and thiophenecarboxylic acids of the present invention are prepared using a variety of synthetic methods, depending upon the substituent R, its position and the hetero atom (O or S) in the ring. As referenced above, many of the compounds are available in the literature, and it is unnecessary to further detail their syntheses here.

(1) 5-Substitutedfuran-2-carboxylic Acids

5-Phenylthiomethylfuran-2-carboxylic acid is prepared by reaction of the anion of thiophenol with methyl or ethyl 5-chloromethylfuran-2-carboxylate followed by hydrolysis. The anionic form of thiophenol is conveniently formed in situ by reaction of thiophenol with sodium hydride in an aprotic solvent (e.g. dimethylformamide, tetrahydrofuran, dimethoxyethane, dimethylsulfoxide) which will not otherwise react with sodium hydride or thiophenoxide under the conditions employed. Once the salt is formed, the choice of solvent for its reaction with the furan derivative becomes less critical. A wide variety of solvents, including water, alcohols, ketones, ethers, halogenated hydrocarbons, acetonitrile, dimethylformamide etc., or miscible combinations thereof, are useful. The only requirements are that the solvent be inert towards reactants and product, that the reactants have some degree of solubility, and that the solvent be less acidic than thiophenol, so as to maintain the anionic form thereof. The temperature employed for this reaction is not critical (e.g. 0°–120° C.). It should be high enough to provide a reasonable rate, but not so high as to lead to undue decomposition. Other displaceable groups (e.g. Br, I, $OSO_2CH_3$, etc.) can be substituted for the chlorine of the furan moiety. As is well known in the art, rate will vary with the nature of the group displaced, the solvent, the temperature and the concentration of reactants. To maximize yields, the reaction time should be such that the reaction is nearly complete (e.g. >95% conversion when equivalent amounts of chloride and cyanide are employed: a few minutes to several days). These reactions are readily monitored by thin layer chromatography, employing one of a variety of commercially available silica gel plates containing an ultraviolet indicator. Suitable eluants are ethyl acetate/hexane mixtures with about 5% added acetic acid. The proportion of these solvents is varied with the polarity of the reactant and product, a practice well known in the art. For example, for the reaction of methyl 5-chloromethylfuran-2-carboxylate, the use of an eluant consisting of 5 parts of hexane, 1 part of ethyl acetate and 5% acetic acid is well suited. The hydrolysis of the lower alkyl esters resulting from the displacement reaction is readily carried out, employing acid or base catalysis, well-known in the chemical art. Conveniently the hydrolysis is carried out in a mixture of aqueous sodium hydroxide and methanol or ethanol by heating for 1–4 hours on a steam bath, under reflux or in an open flask.

Like 5-phenylthiofuran-2-carboxylic acid itself, other 5-thioethers of the present invention (R=phenylthio monosubstituted in the 2-, 3- or 4-position with ($C_1$-$C_3$)alkyl, phenyl, methoxy, chloro, fluoro or trifluoromethyl; phenylthio disubstituted in the 2,5- or 3,5-positions with methyl, methoxy, chloro or fluoro; 2,3,5,6-tetrafluorophenylthio; or ($C_2$-$C_6$)alkylthio) can be prepared by the two-step method of Manly and Amstutz referenced above, by substitution of the appropriate mercaptan for thiophenol. The requisite mercaptans are available commercially, in the literature or by suitable adaptation of literature methods. Alternatively, where the precursor aldehydes are available, these thioether derivatives can be prepared by the method of Kada et al., referenced above.

(2) 5-Substitutedfuran-3-carboxylic Acids

The 5-ether and thioether derivatives of furan-3-carboxylic acid are prepared from 5-bromofuran-3-carboxylic acid and the appropriate alcohol or mercaptan, in the presence of cuprous oxide, in an inert solvent at elevated temperature (120°–175° C.) and under pressure, if necessary, for about 10–50 hours. If desired, the reaction is monitored by thin layer chromatography as described above (for example, for the reaction of 2-methoxythiophenol with 5-bromofuran-3-carboxylic acid, an eluant consisting of 5 parts of hexane, 1 part of ethyl acetate and 5% acetic acid is well suited).

5-Phenylthiomethylfuran-3-carboxylic acid can be prepared by the reaction of thiophenoxide with a lower alkyl 5-halofuran-3-carboxylate [e.g., known ethyl 5-chloromethylfuran-3-carboxylate; Divald et al., J. Org. Chem. 41, 2835 (1976)] followed by hydrolysis of the resulting ester. Methodology and conditions for these reactions are as described above for the preparation of 5-phenylthiomethylfuran-2-carboxylic acid.

(3) 2-Substitutedfuran-3-carboxylic Acids 2-($C_1$-$C_2$)Alkoxy- and 2-phenoxyfuran-3-carboxylic acid can be prepared by applying the 2-stage method of Manly and Amstutz to lower alkyl 2-bromofuran-3-carboxylates. In the first stage intermediate esters are formed by reacting approximately one equivalent of sodium methoxide, sodium ethoxide or sodium thiophenoxide in methanol, ethanol or thiophenol, respectively, with lower alkyl 2-bromofuran-3-carboxylate at 90°–150° C. for 1–5 hours. Without isolation, the esters are hydrolyzed by the addition of aqueous sodium hydroxide and heating on a steam bath for 1–4 hours as detailed above in the preparation of 5-phenylthiomethylfuran-2-carboxylic acid.

2-Benzylfuran-3-carboxylic acid can be prepared by Friedel-Crafts type reaction of known methyl or ethyl 2-bromomethylfuran-3-carboxylate or 2-chloromethylfuran-3-carboxylate [Bisagni and Rivalle, Bull. Soc. Chim. Fr., 519 (1974)] with benzene, followed by hydrolysis. The method of Elliott et al. [J. Chem. Soc. (C), 2551 (1971)], or the like, is suitable for the alkylation step. The hydrolysis conditions are as detailed above for the preparation of 5-phenylthiomethylfuran-2-carboxylate. Alternatively, 2-benzylfuran-3-carboxylate can be prepared by the reduction of known 2-benzoylfuran-3-carboxylic acid [MacDowell and Ballas, J. Org. Chem. 42, 3717 (1977)], for example, with hydrazine in hot potassium hydroxide/ethylene glycol according to the method of specific Example 2 below.

2-Phenylthiomethylfuran-3-carboxylic acid can also be prepared from the halomethylfurans of Bisagni and Rivalle (cited in the paragraph immediately above) following the two-step displacement/hydrolysis procedures detailed above for the preparation of 5-phenylthiofuran-2-carboxylic acid.

The 2-thioether derivatives of furan-3-carboxylic acid (R=phenylthio, substituted phenylthio, naphthylthio or ($C_1$–$C_6$)alkylthio) are prepared by sulfenylation of lithiated furan-3-carboxylic acid. The starting acid is treated in an ether solvent (e.g. tetrahydrofuran) at reduced temperature (e.g. $-20°$ to $-10°$ C.) with two equivalents of butyl lithium in hexane. The appropriate sulfenyl chloride (approximately 2 equivalents) is added and reaction allowed to proceed at higher temperature (e.g. 0°–50° C.) for up to 2 hours. The sulfenyl chlorides are prepared from the corresponding mercaptans or disulfides by the action of a halogenating agent (chlorine or N-chlorosuccinimide). The required mercaptans are available commercially, in the literature, or by suitable adaptation of literature methods.

(4) 5-Substitutedthiophene-2-carboxylic Acids

Like known 5-methoxythiophene-2-carboxylic acid, the 5-ethoxy and phenoxy analogs can be prepared by the method of Sicé (cited in the Background of the Invention), viz., the reaction of methoxide, ethoxide or phenoxide with 2-iodothiophene in the corresponding alcohol/phenol, in the presence of cupric oxide, to yield 2-methoxy, 2-ethoxy and 2-phenoxythiophene, respectively, followed by lithiation and carboxylation. Alternatively, these compounds are prepared by reaction of methoxide, ethoxide or phenoxide with 5-bromothiophene-2-carboxylic acid, employing procedures and conditions as detailed above for the conversion of methyl 5-chloromethylfuran-2-carboxylate to methyl 5-phenylthiomethyl-2-carboxylate. In the present case, however, except where the alcohol/phenol corresponding to the anion is employed as solvent, the solvent should be considerably less acidic than the protonated form of the anion (i.e. methanol, ethanol or phenol).

5-Phenylthiothiophene-2-carboxylic acid can be prepared from known 5-chloro(or bromo)methylthiophene-2-carboxylic acid [Haworth and Jones, J. Chem. Soc., 667 (1944)] by following the two-step procedure detailed above for the synthesis of 5-phenylthiofuran-2-carboxylic acid.

5-Thioether derivatives of thiophene-2-carboxylic acid are readily prepared by reaction of the anionic form of thiophenols/mercaptans with 5-bromothiophene-2-carboxylic acid (the corresponding lower alkyl ester can also be employed, with a hydrolysis step added). The anionic form of the mercaptan/thiophenol is conveniently formed in situ as described above in the preparation of lower alkyl 5-phenylthiomethylfuran-2-carboxylate. Procedures/conditions for the replacement phase of the reaction, as detailed in the latter case, apply here also, except to note that in the present case the reaction is generally slower, requiring higher temperatures (e.g. 140°–200° C.) to achieve a reasonable rate (e.g. reaction time of 2–20 hours). Obviously, the reaction is run under pressure, if necessary, to achieve the desired temperature. In this case, a suitable thin layer chromatographic system for monitoring the reactions is hexane/5% acetic acid as eluant.

(5) 5-Substitutedthiophene-3-carboxylic Acids

5-Ether and 5-thioether derivatives of thiophene-3-carboxylic acids can be prepared from 5-bromothiophene-3-carboxylic acid and the appropriate alcohol by following the procedures detailed above for the preparation of the corresponding 5-ether and 5-thioether derivatives of furan-3-carboxylic acid.

5-Benzylthiophene-3-carboxylic acid can be prepared by hydrolysis of known methyl 5-benzylthiophene-3-carboxylate, [Elliott et al., J. Chem. Soc. (C), 2551 (1971)]. Procedures/conditions are as described above for the preparation of 5-phenylthiomethyl-3-carboxylate.

5-Phenylthiomethylthiophene-3-carboxylic acid can be prepared from known 5-bromomethylthiophene-3-carboxylic acid [Jorda et al., Collect. Czech. Chem. Commun. 41, 1541 (1976)] and thiophenoxide employing the replacement conditions described above for the preparation of methyl 5-phenylthiomethylfuran-2-carboxylate.

(6) 2-Substitutedthiophene-3-carboxylates

2-Ether and 2-thioether derivatives of thiophene-3-carboxylic acid can be prepared from 2-bromothiophene-3-carboxylic acid following procedures detailed above for the preparation of 5-ether and 5-thioether derivatives of thiophene-2-carboxylic acid.

2-Benzylthiophene-3-carboxylic acid can be prepared by the reduction of known 2-benzoylthiophene-3-carboxylic acid following procedures detailed above for the reduction of 2-benzoylfuran-3-carboxylic acid.

The pharmaceutically-acceptable cationic salts of the compounds of the present invention are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of a different salt of the cation (sodium ethylhexanoate, magnesium oleate), employing a solvent in which the desired cationic salt precipitates, or can be otherwise isolated by concentration and addition of a non-solvent.

The furancarboxylic and thiophenecarboxylic acids of the present invention are readily adapted to clinical use as antidiabetic agents. The hypoglycemic activity required for this clinical use is well illustrated by the test procedure which follows. Intact male albino rats, each weighing approximately 200 grams are the experimental test animals employed for such purposes. The test animals are fasted approximately 18–24 hours. The rats are weighed, numbered, and recorded in groups of five or six as needed. Each animal is then dosed with glucose (usually one gram per kilogram) intra-peritoneally, and then either saline (controls) or compound. The treated animals are given the furnacarboxylic or thiophenecarboxylic acid to be tested at a dosage of 100 mg./kg. or less; in each instance, the drug is suspended or dissolved in an aqueous system, and the doses are administered orally or parenterally. Blood glucose is measured over a period of 3 hours in both control and treated groups. The results obtained are expressed in terms of the percentage decrease in the blood glucose value of treated animals from the control value. Those compounds which decrease the blood glucose by 20% or better are considered to have high activity; while those which decrease it by 30% or better are considered to have exceptionally high activity. In this connection, it is significant to note that the results obtained show that the compounds of the present invention exhibit a hypoglycemic effect which is comparable to that afforded by known clinically useful anti-diabetics in this field.

The furancarboxylic and thiophenecarboxylic acids of the present invention are clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg./kg. body weight of the subject per day, preferably about 0.10 to about 10 mg./kg. body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

The compounds can be used in pharmaceutical preparations containing the compound, or a pharmaceutically acceptable acid salt thereof, in combination with a pharmaceutically acceptable carrier or diluent. Suitable pharmaceutically acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically acceptable acid addition salts of the compounds. The injectable solutions prepared in this manner can then be administered intravenously, intraperitoneally, subcutaneously or intramuscularly, with intramuscular administration being preferred in man.

The present invention is illustrated by the following examples. However, it should be understood that the invention is not limited to the specific details of these examples.

EXAMPLE 1

5-Phenylthiomethylfuran-2-carboxylic Acid

Benzenethiol (0.7 ml., 7 mmoles) and sodium hydride (300 mg. of 57% dispersion in oil, 7 mmoles) were dissolved in 10 ml. of dimethylformamide by stirring for 0.5 hour at room temperature. Methyl 5-chloromethylfuran-2-carboxylate [1.2 g., 7 mmoles; Mndzhoyan et al., Doklady Akad. Nauk Armyan. S.S.R. 25, 133 (1957); Chem. Abs. 52, 6306e] was added and the mixture stirred for approximately 16 hours at room temperature. To hydrolyze the methyl-5-phenylthiomethylfuran-2-carboxylate thereby formed in situ, 1 N sodium hydroxide (15 ml.) was added, and the mixture heated on a steam bath for 1 hour. The mixture was cooled, diluted with 20 ml. of water, extracted with 15 ml. of ether, the aqueous phase acidified with concentrated hydrochloric acid, approximately 15 ml. of hexane added and crystalline product recovered by filtration of the two phase system (0.9 g., m.p. 107°–108.5° C.). Recrystallization from ether/hexane afforded purified 5-phenylthiomethylfuran-2-carboxylic acid (690 mg., m.p. 108°–109° C.).

Analysis: Calcd. for $C_{12}H_{10}O_3S$: C, 61.54; H, 4.30. Found: C, 61.73; H, 4.42.

EXAMPLE 2

5-Benzylfuran-2-carboxylic Acid

5-Benzoylfuran-2-carboxylic acid [420 mg.; Knoppova et al. Collect. Czech. Chem. Commun. 42, 3175–9 (1977), Chem. Abs. 88, 169842d] was combined with 10 ml. of hydrazine, 1.5 g. of potassium hydroxide and 10 ml. of ethylene glycol and heated for 1.5 hours in an oil bath maintained at 160° C. The mixture was cooled in an ice-water bath, diluted with water and acidified with conc. hydrochloric acid. Filtration gave 5-benzylfuran-2-carboxylic acid (250 mg., m/e 202).

The same procedure is used to convert 2-benzoylthiophene-3-carboxylic acid [Pirson et al., Bull. Soc. Chim. Belges 79, 575 (1970)] to 2-benzylthiophene-3-carboxylic acid.

5-Benzylfuran-2-carboxylic acid is alternatively prepared by the method of Mndzhoyan et al. [Doklady Akad. Nank Armyan. S.S.R. 25, 133 (1957); Chem. Abstr. 52, 6306], by the method of Tsukervanika and Galustyan [Dokl. Akad. Nank Uz. S.S.R. 20, 26 (1963); Chem. Abs. 59, 6341], or by the method of French Pat. No. 1,578,377 (1969; Chem Abstr. 72, 121350j).

EXAMPLE 3

5-Phenylthiothiophene-2-carboxylic Acid (A) Thiophenol (1.03 ml., 10 mmoles) and sodium hydride (0.42 ml. of 57% dispersion in oil, 10 mmoles) were stirred in 20 ml. of tetrahydrofuran for 30 minutes.

Sodium thiophenolate was recovered by concentration to dryness. 5-Bromothiophene-2-carboxylic acid [1 g., 5 mmoles; Fournari et al., Bull. Soc. Chim. Fr. 4115 (1967)] and 30 ml. of quinoline were added and the mixture heated for 6.5 hours in an oil bath maintained at 210°–212° C. Dimethylsulfoxide (10 ml.) was added to dissolve the gelatinous precipitate which had not dissolved to this point in time, and heating in the 210°–212° C. oil bath continued for 2.5 hours. The reaction mixture was cooled to room temperature, poured onto approximately 150 g. of ice, acidified with conc. hydrochloric acid, and product extracted into ethyl acetate. Product was extracted back into 1 N sodium hydroxide (four 50 ml. portions). The first two extracts were acidified, and product now extracted into ether and concentrated to an oil. The oil was redissolved in ether (10 ml.), excess hydrogen chloride in ethyl acetate added, the solution stripped to semisolids, the semisolids triturated with water, and crystalline product (450 mg.) recovered by filtration. Recrystallization from ether/hexane gave purified 5-phenylthiothiophene-2-carboxylic acid (68 mg., m.p. 83°–88° C.) as a first crop. The mother liquors were evaporated to dryness, taken up in 15 ml. of methanol and crystallization induced by addition of 20 ml. of water to give additional purified product (164 mg., m.p. 93°–95° C.). The second two 1 N sodium hydroxide extracts were acidified, yielding additional crystalline product (57 mg., m.p. 91°–93° C.) directly. Recrystallization of 50 mg. of the latter gave material for analysis. (28 mg., m.p. 93.5°–95° C.).

Analysis: Calcd. for $C_{11}H_8O_2S_2$: C, 55.94; H, 3.41. Found: C, 55.87; H, 3.52.

(B) Thiophenol (6.2 ml., 60 mmoles) and sodium hydride (2.5 g. of 57% in oil, 60 mmoles) were heated at 100° C. in 50 ml. of dimethylsulfoxide for 15 minutes, at which time evolution of hydrogen was complete. 5-Bromothiophene-2-carboxylic acid (6.2 g., 30 mmoles) was added and the mixture heated for 5 hours near reflux in an oil bath maintained at 190°–192° C. The reaction was cooled to room temperature, diluted with 200 ml. of 0.5 N sodium hydroxide and extracted with 75 ml. of ether. The aqueous phase was acidified with conc. hydrochloric acid and product extracted into 100 ml. of ethyl acetate. The extract was back-washed with water, clarified by filtration and concentrated to a waxy solid (4.5 g.). The crude solids were chromatographed on 200 ml. of silica gel with hexane/5% acetic acid as eluant. Later fractions, evaporated to dryness and recrystallized from 1:1 methanol/water gave purified 5-phenylthiothiophene-2-carboxylic acid. (700 mg., m.p. 93.5°–95° C.).

EXAMPLE 4

5-(3-Methylphenylthio)thiophene-2-carboxylic Acid m-Toluenethiol (7.45 g., 60 mmoles) was converted to sodium salt and reacted with 2-bromothiophene-3-carboxylic acid following the procedure of Example 3B. After cooling to room temperature, dilution with base, ether extraction and acidification according to the same Example, crude product was recovered by filtration (3 g.). Two recrystallizations from ether/hexane afforded purified 5-(3-methylphenylthio)thiophene-2-carboxylic acid as a second crop (148 mg., m.p. 73°–75° C.) Recrystallization of the first crop (1.2 g.) from 1:1 methanol/water gave, again as a second crop, additional purified product (70 mg., m.p. 72°–74° C.).

Analysis: Calcd. for $C_{12}H_{10}O_2S_2$: C, 57.60; H, 4.03. Found: C, 57.40; H, 3.95.

EXAMPLE 5

5-(3-Chlorophenylthio)thiophene-2-carboxylic Acid

3-Chlorothiophenyl (8.7 g., 60 mmoles) was converted to sodium salt and reacted with 5-bromothiophene-2-carboxylic acid according to the procedure of Example 3B. After cooling, base dilution, ether extraction and acidification according to the same Example, a gum was isolated by decantation from the acidified aqueous phase. The gum was taken up in 50 ml. of methanol, clarified by filtration, diluted with 200 ml. of water and the product extracted into 75 ml. of ether. The ether extract was back-washed with water and evaporated to an oil (3.8 g.). The oil was triturated with hot hexane, extracted into 30 ml. of 1 N sodium hydroxide and crystalline product (1.6 g.) recovered by filtration. Two recrystallizations from ether/hexane gave purified 5-(3-chlorophenylthio)thiophene-2-carboxylic acid (556 mg., m.p. 112°–115° C.).

Analysis: Calcd. for $C_{11}H_7O_2S_2Cl$: C, 48.79; H, 2.61. Found: C, 49.02; H, 2.75.

EXAMPLE 6

5-(4-Chlorophenylthio)thiophene-2-carboxylic Acid

By the procedure of Example 3B, 4-chlorothiophenol (8.7 g., 60 mmoles) was converted to its sodium salt and reacted with 5-bromothiophene-2-carboxylic acid. Cooling, base addition, ether extraction, and acidification, according to Example 3B, but adding a clarification step prior to acidification, gave crystalline product (2.5 g.) directly. Two recrystallizations from 2:1 methanol/water and one recrystallization from ether/hexane gave purified 5-(4-chlorophenylthio)thiophene-2-carboxylic acid (420 mg., m.p. 158°–160° C.).

Analysis: Calcd. for $C_{11}H_7O_2S_2Cl$: C, 48.79; H, 2.61. Found: C, 48.79; H, 2.68.

By the same procedure, from the appropriate thiophenol and 5-bromothiophene-2-carboxylic acid the following additional thiophene carboxylic acids are prepared:

5-(2-Methylphenylthio)thiophene-2-carboxylic acid;
5-(4-Methylphenylthio)thiophene-2-carboxylic acid;
5-(3,5-Dimethylphenylthio)thiophene-2-carboxylic acid;
5-(2-Isopropylphenylthio)thiophene-2-carboxylic acid;
5-(2-Methoxyphenylthio)thiophene-2-carboxylic acid;
5-(4-Methoxyphenylthio)thiophene-2-carboxylic acid;
5-(2-Chlorophenylthio)thiophene-2-carboxylic acid;
5-(2,5-Dichlorophenylthio)thiophene-2-carboxylic acid;
5-(3,5-Dichlorophenylthio)thiophene-2-carboxylic acid;
5-(2-Fluorophenylthio)thiophene-2-carboxylic acid;
5-(3-Fluorophenylthio)thiophene-2-carboxylic acid;
5-(2,5-Difluorophenylthio)thiophene-2-carboxylic acid;
5-(3,5-Difluorophenylthio)thiophene-2-carboxylic acid;
5-(3-Trifluoromethylphenylthio)thiophene-2-carboxylic acid;
5-(2-Naphthylthio)thiophene-2-carboxylic acid and
5-Pentylthiothiophene-2-carboxylic acid.

By substituting an equivalent of sodium methoxide, sodium ethoxide or sodium phenoxide for the sodium salt of thiophenol in the procedure of Examples 3B, 4, 5 and 6, the following compounds are produced, respectively:

5-Methoxythiophene-2-carboxylic acid;
5-Ethoxythiophene-2-carboxylic acid and
5-Phenoxythiophene-2-carboxylic acid.

The latter compounds are alternatively prepared by reaction of 2-iodothiophene with methoxide, ethoxide or phenoxide, followed by carbonylation according to Sice' [J. Am. Chem. Soc. 75, 3697 (1953)], or by alkylation of 5-hydroxythiophene-2-carboxylic acid by the method of Gronowitz [Ankiv Kemi 12, 239 (1958); Chem. Abstr. 52, 20115].

By substituting an equivalent of sodium methoxide, sodium ethoxide or sodium phenoxide for the sodium salt of the thiols of Examples 3B, 4, 5 and 6 and substituting an equivalent amount of 2-bromothiophene-3-carboxylic acid for 5-bromothiophene-3-carboxylic acid, the following compounds are prepared:

2-Methoxythiophene-3-carboxylic acid;
2-Ethoxythiophene-3-carboxylic acid and
2-Phenoxythiophene-3-carboxylic acid.

EXAMPLE 7

5-Benzylthiophene-2-carboxylic Acid

5-Benzoylthiophene-2-carboxylic acid (1.2 g.) was combined with potassium hydroxide (4 g.), hydrazine (3 ml.) and ethylene glycol (8 ml.) and heated in a 140° C. oil bath. A thick, foamy slurry formed which was diluted with 10 ml. additional ethylene glycol. The bath temperature was increased to 180° C., and the reaction held at this temperature for 45 minutes. The reaction was cooled, filtered and the filtrate diluted with 75 ml. of water. The mixture was cooled in an ice bath, acidified with conc. hydrochloric acid, and product (658 mg.) recovered by filtration. Recrystallization from methanol/water gave purified 5-benzylthiophene-2-carboxylic acid (480 mg., 123°–125° C., m/e 218).

Analysis: Calcd. for $C_{12}H_{10}O_2S$: C, 66.03; H, 4.61. Found: C, 66.33; H, 4.64.

The same compound is alternatively prepared by the method of MacDowell and Patrick [J. Org. Chem. 32, 2441 (1967)].

EXAMPLE 8

5-Phenylthiofuran-3-carboxylic Acid

In an open flask, thiophenol (2.86 g., 13 mmoles), cuprous oxide (1.86 g., 13 mmoles) and dimethyl formamide (30 ml.) were combined and heated in a 135° C. oil bath. The reaction mixture was allowed to cool slightly, 5-bromothiophene-3-carboxylic acid [2.5 g., 13 mmoles; Fournari et al., Bull. Chim. Soc. Fr., 4115 (1967)] in 50 ml. of dimethylformamide was added, and the mixture refluxed for 2 days. The reaction mixture was cooled, clarified by filtration, the filtrate evaporated to an oil, the oil triturated with 1 N hydrochloric acid, and gummy solids recovered by filtration and taken up in 1 N sodium hydroxide. The basic solution was extracted with ether, reacidified with conc. hydrochloric acid, product recovered by filtration, triturated with hexane and refiltered (912 mg., m.p. 97°–100° C., m/e 220). Recrystallization from methanol/water afforded purified 5-phenylthiofuran-3-carboxylic acid (439 mg., m.p. 101°–103° C.).

Analysis: Calcd. for $C_{11}H_8O_3S$: C, 59.98; H, 3.66. Found: C, 59.69; H, 3.80.

EXAMPLE 9

5-(2-Methylphenylthio)furan-3-carboxylic Acid

In an open flask cuprous oxide (2.25 g., 15.7 mmoles) and o-toluenethiol (3.89 g., 31.4 mmoles) were combined in 40 ml. of dimethylformamide and heated in a 150° C. oil bath until a thick yellow mixture formed. The mixture was cooled slightly and 5-bromofuran-3-carboxylic acid [3.0 g., 15.7 mmoles; Gilman and Burtner, J. Am. Chem. Soc. 55, 2903 (1933)] in 40 ml. of dimethylformamide added. The mixture was heated in a 175° C. oil bath for approximately 16 hours. The reaction mixture was cooled, solids removed by filtration, the filtrate diluted with 500 ml. of water, acidified with 6 N hydrochloric acid and product extracted into three portions of ethyl acetate. The ethyl acetate extracts were combined, evaporated to an oil, the oil taken up in 1 N sodium hydroxide, the basic solution washed with ether, cooled, reacidified and product (650 mg.) recovered by filtration. Recrystallization from methanol/water gave purified 5-(2-methylphenylthio)furan-3-carboxylic acid (485 mg., m.p. 148°–150° C., m/e 234).

Analysis: Calcd. for $C_{12}H_{10}O_3S$: C, 61.52; H, 4.30. Found: C, 61.89; H, 4.48.

EXAMPLE 10

5-(3-Methylphenylthio)furan-3-carboxylic Acid m-Toluenethiol (3.8 g., 30 mmoles) and cuprous oxide (2.2 g., 15.5 mmoles) were combined in 40 ml. of dimethylformamide and heated with stirring in a 170°–175° C. oil bath in an open flask for 1 hour. A thick precipitate formed. The mixture was diluted with 20 ml. dimethylformamide and heating continued for an additional 0.5 hour. 5-Bromofuran-3-carboxylic acid (2.6 g., 13.6 mmoles) in 100 ml. of dimethylformamide was added and heating at 160°–165° C. (bath temperature) continued for approximately 16 hours. The mixture was cooled to room temperature, diluted with 500 ml. of water, acidified with hydrochloric acid and product extracted into two 250 ml. portions of ethyl acetate. The extracts were combined, back-washed with water and concentrated to an oil (3 g.). The oil was chromatographed on approximately 150 ml. of silica gel with hexane/5% acetic acid as eluant. Slowest moving, product-containing fractions were combined, evaporated to dryness, taken up in hexane, solids removed by filtration, the filtrate evaporated to dryness and product (825 mg.) crystallized by trituration with water. Recrystallization from ether/hexane gave purified 5-(3-methylphenylthio)furan-3-carboxylic acid (443 mg., m.p. 52°–54° C., m/e 234).

Analysis: Calcd. for $C_{12}H_{10}O_3S \cdot 0.4 H_2O$: C, 59.70; H, 4.50. Found: C, 59.56; H, 4.21.

EXAMPLE 11

5-(4-Methylphenylthio)furan-3-carboxylic Acid

Using reagent quantities identical to that of Example 9, p-toluenethiol and cuprous oxide were combined in 45 ml. of dimethylformamide heated at 135° C. for about 1.5 hours, cooled somewhat, 5-bromofuran-3-carboxylic acid in 40 ml. of dimethylformamide added, and the mixture refluxed for 24 hours. Crude product (185 mg.) was recovered according to the procedure of Example 10. Recrystallization from methanol/water afforded purified 5-(4-methylphenylthio)furan-3-carboxylic acid (135 mg., m.p. 116°–119° C.).

Analysis: Calcd. for $C_{12}H_{10}O_3S$: C, 61.52; H, 4.30. Found: C, 61.77; H, 4.45.

By the same process, an equivalent amount of p-isopropylthiophenol [Gliman and Broadbent, J. Am. Chem. Soc. 69, 2054 (1947)] is converted to:

5-(4-Isopropylphenylthio)furan-3-carboxylic acid.

EXAMPLE 12

5-(2-Isopropylphenylthio)furan-3-carboxylic Acid

Following the procedure of Example 9, o-isopropylthiophenol [4.77 g., 31.4 mmoles; Hansch and Blondon, J. Am. Chem. Soc. 70, 1561 (1948)] was reacted with 5-bromofuran-3-carboxylic acid. Rather than recover the initial crude product by filtration, the mixture was reextracted with ethyl acetate, the ethyl acetate back-washed with water and saturated brine, dried over anhydrous sodium sulfate and evaporated to yield crude product. Recrystallization from hexane produced purified 5-(2-isopropylphenylthio)furan (785 mg., m.p. 117°–120° C., m/e 262).

Analysis: Calcd. for $C_{14}H_{14}O_3S$: C, 64.09; H 5,37. Found: C, 64.22; H, 5.44.

By the same procedure, o-ethylthiophenol and o-propylthiophenol [Hansch and Blondon, loc. cit.] are converted, respectively, to:

5-(2-ethylphenylthio)furan-3-carboxylic acid and
5-(2-propylphenylthio)furan-3-carboxylic acid.

EXAMPLE 13

5-(3,5-Dimethylphenylthio)furan-3-carboxylic Acid 3,5-Dimethylthiophenol (4.33 g., 31.4 mmoles; prepared from 3,5-dimethylaniline by the procedures of Tarbell and Fukushima, Org. Synth. III, 809) and cuprous oxide (2.25 g., 15.7 mmoles) were reacted in 40 ml. of dimethylformamide at 140° C. for three hours. The mixture was cooled slightly and 5-bromofuran-3-carboxylic acid (3.0 g., 15.7 mmoles) in 40 ml. of dimethylformamide added. The mixture was refluxed for approximately 16 hours. Isolation of crude product as an oil was according to the procedure of Example 16 below. The oil was chromatographed on silica gel with ethyl acetate-1/hexane-5/5% acetic acid as eluant. Product was recovered by evaporation of clean, middle fractions and trituration with water (706 mg.). Recrystallization from methanol/water gave purified 5-(3,5-dimethylphenylthio)furan-3-carboxylic acid (440 mg., m.p. 82°–86° C., m/e 248).

Analysis: Calcd. for $C_{13}H_{12}O_3S$: C, 62.88; H, 4.87. Found: C, 63.14; H, 4.93.

EXAMPLE 14

5-(2-Methoxyphenylthio)furan-3-carboxylic Acid

Following the procedure of Example 9, except that a total of 100 ml. of dimethylformamide was employed, o-methoxythiophenol (4.39 g., 31.4 mmoles) was reacted with 5-bromofuran-3-carboxylic acid to yield 1.84 g. of crude product. Recrystallization from methanol/water, which included decolorization with activated carbon, afforded purified 5-(2-methoxyphenylthio)furan-3-carboxylic acid (1.3 g., m.p. 138°–141° C., m/e 250).

Analysis: Calcd. for $C_{12}H_{10}O_4S$: C, 57.58; H, 4.02. Found: C, 57.88; H, 4.20.

By the same procedure, m-methoxythiophenol is converted to:

5-(3-Methoxyphenylthio)furan-3-carboxylic acid.

EXAMPLE 15

5-(4-Methoxyphenylthio)furan-3-carboxylic Acid

By the procedure of Example 11, p-methoxythiophenol (4.39 g., 31.4 mmoles) and cuprous oxide (2.25 g., 15.7 mmoles) heated at 135° C. for 2 hours were reacted with 5-bromofuran-3-carboxylic acid (3 g., 15.7 mmoles) in 60 ml. of dimethylformamide, and crude product (1.67 g. ) isolated. Recrystallization from methylene chloride/hexane gave purified 5-(4-methoxphenylthio)furan-3-carboxylic acid (825 mg., m.p. 115°–117° C., m/e 250).

Analysis: Calcd. for $C_{12}H_{10}O_4S$: C, 57.58; H, 4.02. Found: C, 57.74; H, 4.15.

EXAMPLE 16

5-(2-Chlorophenylthio)furan-3-carboxylic Acid o-Chlorothiophenol (4.5 g., 31 mmoles) and cuprous oxide (2.2 g., 15.5 mmoles) in 100 ml. of dimethylformamide were heated in an oil bath at 170°–175° C. for 1.5 hours, during which time a precipitate formed. 5-Bromofuran-3-carboxylic acid (3 g., 15.7 mmoles) was added and heating continued for 2.5 hours. The reaction mixture was cooled to room temperature, filtered, diluted with 500 ml. of water, acidified with conc. hydrochloric acid and product extracted into 250 ml. of ethyl acetate. The ethyl acetate was back-washed with 150 ml. of water and insolubles removed by filtration. Product was extracted from the ethyl acetate into 150 ml. of 1 N sodium hydroxide, the aqueous phase acidified with conc. hydrochloric acid and product reextracted into 150 ml. of fresh ethyl acetate. The ethyl acetate was back-washed with water and concentrated to an oil (3.5 g.). Recrystallization from ether/hexane gave partially purified product in two crops (575 mg., 403 mg.). These were combined and chromatographed on approximately 150 ml. of silica gel with hexane/5% acetic acid as eluant. Middle fractions afforded purified 5-(2-chlorophenylthio)furan-3-carboxylic acid (490 mg., m.p. 146°–148° C., m/e 254).

Analysis: Calcd. for $C_{11}H_7O_3SCl$: C, 51.87; H, 2.77. Found: C, 51.81; H, 2.91.

EXAMPLE 17

5-(3-Chlorophenylthio)furan-3-carboxylic Acid

Following the procedure of Example 11, except for use of two 50 ml. quantities of dimethylformamide, 3-chlorothiophenol (4.52 g., 31.4 mmoles) was reacted with 5-bromofuran-3-carboxylic acid to yield crude product (1.9 g.). Recrystallization from hot hexane gave purified 5-(3-chlorophenylthio)furan-3-carboxylic acid (1.0 g., m.p. 98°–102° C., m/e 254).

Analysis: Calcd. for $C_{11}H_7O_3SCl$; C, 51.87; H, 2.77. Found: C, 51.69; H, 2.93.

EXAMPLE 18

5-(4-Chlorophenylthio)furan-3-carboxylic Acid p-Chlorothiophenol (4.52 g., 31.4 mmoles) was reacted with 5-bromo-furan-3-carboxylic acid according to the procedure of Example 15, except that the total volume of dimethylformamide was 85 ml., and the reflux period was 8 hours. The reaction mixture was cooled, filtered, the filtrate diluted with 500 ml. of water and insolubles removed by filtration. The latter filtrate was made acidic with 6 N hydrochloric acid, product was extracted into ethyl acetate and recovered by evaporation to an oil, crystallized by trituration with water (860 mg.). Two crystallizations from methanol/water gave purified 5-(4-chlorophenylthio)furan-3-carboxylic acid (150 mg., m.p. 142°–145° C., m/e 254).

Analysis: Calcd. for $C_{11}H_7O_3SCl$; C, 51.87; H, 2.77. Found: C, 51.97; H, 2.99.

EXAMPLE 19

5-(2,5-Dichlorophenylthio)furan-3-carboxylic Acid

Following the procedure of Example 9, 2,5-dichlorothiophenol (5.62 g., 31.4 mmoles) was reacted with 5-bromothiophene-3-carboxylic acid to yield crude product (1.4 g.). Recrystallization from methanol/water gave purified 5-(2,5-Dichlorophenylthio)furan-3-carboxylic acid (875 mg., m.p. 172°–175° C.).

Analysis: Calcd. for $C_{11}H_6O_3SCl_2$: C, 45.69; H, 2.08. Found: C, 45.52; H, 2.30.

EXAMPLE 20

5-(3,5-Dichlorophenylthio)furan-3-carboxylic Acid

Following the procedure of Example 13, 3,5-dichlorothiophenol (3.4 g., 18 mmoles; prepared from 3,5-dichloroaniline according to the procedures of Tarbell and Fukishima, Org. Synth. III, 809) was reacted with cuprous oxide (1.28 g., 9 mmoles) in 30 ml. of dimethylformamide and then further reacted with 5-bromofuran-3-carboxylic acid (1.7 g., 9 mmoles) in 30 ml. of dimethylformamide. Isolation according to Example 16 gave crude product as an oil. Chromatography on silica gel with ethyl acetate-1/hexane-5/5% acetic acid as eluant gave, by combination and evaporation of clean middle fractions, solid product (461 mg.). Recrystallization from methylene chloride/hexane afforded purified product (280 mg., m.p. 146°–148° C.).

Analysis: Calcd. for $C_{11}H_6O_3SCl_2$; C, 45.69; H, 2.08. Found: C, 45.97; H, 2.41.

EXAMPLE 21

5-(2-Fluorophenylthio)furan-3-carboxylic Acid

Following the procedure of Example 13, o-fluorothiophenol (4.02 g., 31.4 mmoles) was reacted with 5-bromofuran-3-carboxylic acid. Isolation according to the procedure of Example 16 gave crude product as an oil. The product was chromatographed on silica gel with ethyl acetate-1/hexane-5/5% acetic acid as eluant. Combination of clean middle cuts, evaporation to dryness and recrystallization from methanol/water gave purified 5-(2-fluorophenylthio)furan-3-carboxylic acid (266 mg., m.p. 100°–103° C., m/e 238).

Analysis: Calcd. for $C_{11}H_7O_3SF$: C, 55.45; H, 2.95. Found: C, 55.45; H, 3.26.

EXAMPLE 22

5-(3-Fluorophenylthio)furan-3-carboxylic Acid

By the procedure of Example 13, m-fluorothiophenol (3.0 g., 23.4 mmoles) was reacted with cuprous oxide (1.67 g., 11.7 mmoles) in 30 ml. of dimethylformamide and then reacted further with 5-bromofuran-3-carboxylic acid in 30 ml. of dimethylformamide. Isolation of crude solids (920 mg.) was according to Example 9. Recrystallization from methanol/water, which included decolorization with activated carbon, gave purified 5-(3-fluorophenylthio)furan-3-carboxylic acid (500 mg., m.p. 101°–103° C., m/e 238).

Analysis: Calcd. for $C_{11}H_7O_3Sf$: C, 55.45; H, 2.95. Found; C, 55.57; H, 3.17.

EXAMPLE 23

5-(4-Fluorophenylthio)furan-3-carboxylic Acid

Following the procedure of Example 9, p fluorothiophenol (4.02 g., 31.4 mmoles) was reacted with 5-bromofuran-3-carboxylic acid. After refluxing approximately 16 hours, crude product (1.3 g.) was isolated according to the same Example. Recrystallization from methanol/water, including decolorization with activated carbon, gave purified 5-(4-fluorophenyl)furan-3-carboxylic acid (780 mg., m.p. 128°–130° C., m/e 238).

Analysis: Calcd. for $C_{11}H_7O_3SF$: C, 55.45; H, 2.95. Found: 55.66; H. 3.16.

EXAMPLE 24

5-(2,5-Difluorophenylthio)furan-3-carboxylic Acid

Following the procedure of Example 22, 2,5-difluorothiophenol (2.8 g., 19 mmoles) was reacted with cuprous oxide (1.35 g., 9.5 mmoles) and then with 5-bromofuran-3-carboxylic acid to yield crude product (1.07 g.). Two recrystallizations from methanol/water and then recrystallization from methylene chloride/hexane gave purified 5-(2,5-difluorophenylthio)furan-3-carboxylic acid (300 mg., m.p. 143°–145° C., m/e 256).

Analysis: Calcd. for $C_{11}H_6O_3SF_2$: C, 51.36; H, 2.34. Found: C, 51.49; H, 2.52.

EXAMPLE 25

5-(3,5-Difluorophenylthio)furan-3-carboxylic Acid

In an open flask, cuprous oxide (0.6 g., 4 mmoles) and 3,5-difluorothiophenol (0.76 g., 4 mmoles) were combined with 25 ml. of dimethylformamide and heated in an oil bath maintained at 150°–160° C. for 2 hours. 5-Bromofuran-3-carboxylic acid was added, the flask was equipped with a reflux condenser, and heating at 150°–155° C. was continued for 16 hours. The reaction mixture was cooled, filtered, the filtrate diluted with 150 ml. of water and product extracted into two 30 ml. portions of ethyl acetate. The combined ethyl acetate extracts were back-washed with water, evaporated to an oil, the oil taken up in ether, product extracted into 12 ml. of 1 N sodium hydroxide, the basic extract acidified with conc. hydrochloric acid and the product extracted back into fresh ether and evaporated to yield crude product as an oil. The oil was chromatographed on approximately 100 ml. of silica gel with hexane/5% acetic acid as eluant, clean fractions (Rf 0.2 on thin layer chromatography with the same eluant) were combined, concentrated to dryness, and crystallized by trituration with hexane to yield purified 5-(3,5-difluorophenylthio)furan-3-carboxylic acid (127 mg., m.p. 128°–130° C., m/e 256).

Analysis: Calcd. for $C_{11}H_6O_3Sf_2$: C, 51.36; H, 2.34. Found: C, 51.54; H, 2.51.

EXAMPLE 26

5-(2,3,5,6-Tetrafluorophenylthio)furan-3-carboxylic Acid

In an open flask, cuprous oxide (1.95 g., 13.7 mmoles) was combined with 2,3,5,6-tetrafluorothiophenol (5.0 g., 27.4 mmoles) in 40 ml. of dimethylformamide and heated at 140° C. for 2 hours. The reaction was cooled, 5-bromofuran-3-carboxylic acid (2.62 g., 13.7 mmoles) in 50 ml. of dimethylformamide was added, the reaction mixture refluxed for 2 hours, and product (2.75 g.) isolated according to the procedure of Example 9. Recrystallization from methanol/water gave purified 5-(2,3,5,6-tetrafluorophenylthio)furan-3-carboxylic acid (1.78 g., m.p. 150°–153° C., m/e 292).

Analysis: Calcd. for $C_{11}H_4O_3SF_4$: C, 45.21; H, 1.37. Found: C, 45.18; H, 1.61.

EXAMPLE 27

5-(2-Methyl-5-fluorophenylthio)furan-3-carboxylic Acid

In an open flask cuprous oxide (500 mg., 3.5 mmoles) and 2-methyl-5-fluorothiophenol (1.0 g., 7 mmoles) were combined in 35 ml. of dimethylformamide and heated in an oil bath at 135°–140° C. for 2.5 hours. The mixture was cooled slightly, 5-bromofuran-3-carboxylic acid (668 mg., 3.5 mmoles) was added and the mixture refluxed for approximately 16 hours. Crude product was isolated according to Example 16. The resulting oil was crystallized by trituration with water (170 mg.). Recrystallization from methanol/water gave purified 5-(2-methyl-5-fluorophenylthio)furan-3-carboxylic acid (125 mg., m.p. 150°–152° C., m/e 252).

Analysis: Calcd. for $C_{12}H_9O_3SF$: C, 57.13; H, 3.59. Found: C, 57.43; H, 3.87.

EXAMPLE 28

5-(3-Trifluoromethylphenylthio)furan-3-carboxylic Acid

By the procedure of Example 13, m-trifluoromethylthiophenol (5.59 g., 31.4 mmoles) was reacted with 5-bromofuran-3-carboxylic acid. Isolation according to Example 16 gave crude product (1.0 g.) as a gummy solid. The latter was chromatographed on silica gel with ethyl acetate-1/hexane-5/5% acetic acid as eluant. Clean middle fractions were combined and evaporated to solid product (550 mg.). Recrystallization from hexane gave purified 5-(3-trifluoromethylphenylthio)furan-3-carboxylic acid (310 mg., m.p. 99°–101° C., m/e 288).

Analysis: Calcd. for $C_{12}H_7O_3SF_3$: C, 50.00; H, 2.44. Found: C, 50.08; H, 2.61.

EXAMPLE 29

5-Pentylthiofuran-3-carboxylic Acid

1-Pentanthiol (4.8 ml., 31 mmoles) and cuprous oxide (2.2 g., 15.5 mmoles) were combined with 70 ml. of dimethylformamide in an open flask and heated in a 165°–170° C. oil bath for 3 hours. 5-Bromofuran-3-carboxylic acid (2 g., 15.5 mmoles) was added, the flask was equipped with a condenser, and heating at 165°–170° C. was continued for 3.5 hours. Crude product was isolated as an oil (1.7 g.) according to the procedure of Example 16. The oil was chromatographed on approximately 150 ml. of silica gel with hexane/5% acetic acid as eluant. Fractions of 8 ml. volume were collected. Fractions 46 to 50 were combined and concentrated to dryness, yielding product as a semisolid. Vacuum sublimation gave purified 5-pentylthiofuran-3-carboxylic acid (327 mg., s.p. 140° C./0.1 mm., m/e 214).

Analysis: Calcd. for $C_{10}H_{14}O_3S$: C, 56.07; H, 6.59. Found: C, 55.86; H, 6.52.

By the same procedure, an equivalent amount of 1-hexanethiol, 1-butanethiol, 2-butanethiol, 1-propanethiol or 2-propanethiol is reacted with 5-bromofuran-3-carboxylic acid to produce, respectively:

5-Hexylthiofuran-3-carboxylic acid;
5-Butylthiofuran-3-carboxylic acid;
5-(2-Butylthio)furan-3-carboxylic acid;
5-Propylthiofuran-3-carboxylic acid; and
5-Isopropylthiofuran-3-carboxylic acid.

EXAMPLE 30

5-(1-Naphthylthio)furan-3-carboxylic Acid

Following the procedure of Example 9, except that a total volume of 90 ml. of dimethylformamide was used, 1-thionaphthol (5.02 g., 31.4 mmoles) was reacted with 5-bromofuran-3-carboxylic acid. Crude product was isolated as an oil according to Example 16. The oil was solidified by trituration with water (988 mg.). Recrystallization from hexane gave purified 5-(1-naphthylthio)furan-3-carboxylic acid (250 mg., m.p. 118°–120° C., m/e 270).

Analysis: Calcd. for $C_{15}H_{10}O_3S$: C, 66.65; H, 3.72. Found: C, 66.66; H, 3.94.

By the same procedure the same amount of 2-thionaphthol and equivalent amounts of 2-, 3- and 4-phenylthiophenol are converted to, respectively:

5-(2-Naphthylthio)furan-3-carboxylic acid;
5-(2-Biphenylthio)furan-3-carboxylic acid;
5-(3-Biphenylthio)furan-3-carboxylic acid; and
5-(4-Biphenylthio)furan-3-carboxylic acid.

An equivalent amount of methanol, ethanol or phenol is substituted for 1-thionaphthol in this procedure to produce, respectively:

5-Methoxyfuran-3-carboxylic acid;
5-Ethoxyfuran-3-carboxylic acid; and
5-Phenoxyfuran-3-carboxylic acid.

In the procedures of Examples 8–30, 5-bromo-thiophene-3-carboxylic acid [Fournari, Bull. Soc. Chim. Fr., 4115 (1967)] is substituted for 5-bromofuran-3-carboxylic acid to produce the following compounds:

5-Phenylthiothiophene-3-carboxylic acid;
5-(2-Methylphenylthio)thiophene-3-carboxylic acid;
5-(3-Methylphenylthio)thiophene-3-carboxylic acid;
5-(4-Methylphenylthio)thiophene-3-carboxylic acid;
5-(2-Isopropylphenylthio)thiophene-3-carboxylic acid;
5-(3,5-Dimethylphenylthio)thiophene-3-carboxylic acid;
5-(2-Methoxyphenylthio)thiophene-3-carboxylic acid;
5-(2-Chlorophenylthio)thiophene-3-carboxylic acid;
5-(3-Chlorophenylthio)thiophene-3-carboxylic acid;
5-(2,5-Dichlorophenylthio)thiophene-3-carboxylic acid;
5-(3,5-Dichlorophenylthio)thiophene-3-carboxylic acid;
5-(2-Fluorophenylthio)thiophene-3-carboxylic acid;
5-(3-Fluorophenylthio)thiophene-3-carboxylic acid;
5-(4-Fluorophenylthio)thiophene-3-carboxylic acid;
5-(2,5-Difluorophenylthio)thiophene-3-carboxylic acid;
5-(3,5-Difluorophenylthio)thiophene-3-carboxylic acid;
5-(2,3,5,6-Tetrafluorophenylthio)thiophene-3-carboxylic acid;
5-(2-Methyl-5-fluorophenylthio)thiophene-3-carboxylic acid;
5-(3-Trifluoromethylphenylthio)thiophene-3-carboxylic acid;

5-Pentylthiothiophene-3-carboxylic acid; and
5-(2-Naphthylthio)thiophene-3-carboxylic acid.

EXAMPLE 31

2-Phenylthiofuran-3-carboxylic Acid

Furan-3-carboxylic acid (1.1 g., 10 mmoles) was dissolved in 30 ml. of tetrahydrofuran and cooled to −10° C. While maintaining the temperature between −10° and 0° C., butyl lithium in hexane (9 ml., 2.22 M, 20 mmoles) was added. The reaction was allowed to warm to room temperature (approximately 20 minutes) and recooled to −10° C. Phenyl sulfenyl chloride solution (estimated 20 mmoles, as a tetrahydrofuran solution, Preparation 4) was added while again maintaining the temperature between −10° and 0° C. After warming the reaction mixture to room temperature and stirring for 1 hour, water (20 ml.) and ether (25 ml.) were added. The organic phase was separated and washed with an additional 20 ml. of water. The combined aqueous phase and water wash were acidified with conc. hydrochloric acid and the product extracted into 25 ml. of fresh ether. The ether extract was back-washed with water and evaporated to yield crude product (1.5 g., solid, m/e 220). The crude was chromatographed on silica gel with hexane/5% acetic acid as eluant. The slower-eluting, clean fractions of product were combined, evaporated to dryness and triturated with hexane to yield purified 2-phenylthiofuran-3-carboxylic acid (180 mg., m.p. 144°–146° C.).

Analysis: Calcd. for $C_{11}H_8O_3S$: C, 60.00; H, 3.66. Found: C, 59.97; H, 3.79.

By the same process the other sulfenylchlorides of Preparations 4–14 are reacted with furan-3-carboxylic acid to yield:

2-(1-Naphthylthio)furan-3-carboxylic acid;
2-(2-Naphthylthio)furan-3-carboxylic acid;
2-(2-Methylphenylthio)furan-3-carboxylic acid;
2-(3-Methylphenylthio)furan-3-carboxylic acid;
2-(4-Methylphenylthio)furan-3-carboxylic acid;
2-(2-Chlorophenylthio)furan-3-carboxylic acid;
2-(3-Chlorophenylthio)furan-3-carboxylic acid;
2-(4-Chlorophenylthio)furan-3-carboxylic acid;
2-(2-Fluorophenylthio)furan-3-carboxylic acid;
2-(3-Fluorophenylthio)furan-3-carboxylic acid;
2-(4-Fluorophenylthio)furan-3-carboxylic acid;
2-(2-Methoxyphenylthio)furan-3-carboxylic acid;
2-(3-Methoxyphenylthio)furan-3-carboxylic acid;
2-(4-Methoxyphenylthio)furan-3-carboxylic acid;
2-(3-Trifluoromethylphenylthio)furan-3-carboxylic acid;
2-(2,5-Dichlorophenylthio)furan-3-carboxylic acid;
2-Methylthiofuran-3-carboxylic acid;
2-Ethylthiofuran-3-carboxylic acid;
2-Butylthiofuran-3-carboxylic acid; and
2-Pentylthiofuran-3-carboxylic acid.

EXAMPLE 32

2-Phenylthiothiophene-3-carboxylic Acid

Thiophene-3-carboxylic acid (1.3 g., 10 mmoles) was dissolved in 35 ml. of tetrahydrofuran, cooled to −10° C. and butyl lithium in hexane (18 ml. of 2.22 M, 40 mmoles) added while maintaining the temperature between −10° and 0° C. The mixture was warmed to room temperature for approximately 0.5 hour. The resulting solution was again chilled to −10° C. and phenylsulfenyl chloride (estimated 40 mmoles in tetrahydrofuran solution (Preparation 1) was added while maintaining the temperature between −10° and 0° C. The reaction was warmed to room temperature and stirred for 2 hours. Water (50 ml.) and ether (50 ml.) were then added. The aqueous phase was separated, acidified with conc. hydrochloric acid and product extracted into fresh ether. The ether extract was back-washed with water and evaporated to crude product (1.8 g., solid). Recrystallization from methanol/water and then from acetone/hexane gave purified 2-phenylthiothiophene-3-carboxylic acid (300 mg., m.p. 159°–161° C.).

Analysis: Calcd. for $C_{11}H_8O_2S_2$: C, 55.94; H, 3.41. Found: C, 55.80; H, 3.48.

A second crop (250 mg., m.p. 158°–160° C.) was also obtained.

By the same procedure, the other sulfenyl chlorides of Preparations 4–15 are reacted with thiophene-3-carboxylic acid to yield:

2-(1-Naphthylthio)thiophene-3-carboxylic acid;
2-(2-Naphthylthio)thiophene-3-carboxylic acid;
2-(2-Methylphenylthio)thiophene-3-carboxylic acid;
2-(3-Methylphenylthio)thiophene-3-carboxylic acid;
2-(4-Methylphenylthio)thiophene-3-carboxylic acid
2-(2-Chlorophenylthio)thiophene-3-carboxylic acid;
2-(3-Chlorophenylthio)thiophene-3-carboxylic acid;
2-(4-Chlorophenylthio)thiophene-3-carboxylic acid;
2-(2-Fluorophenylthio)thiophene-3-carboxylic acid;
2-(3-Fluorophenylthio)thiophene-3-carboxylic acid;
2-(4-Fluorophenylthio)thiophene-3-carboxylic acid;
2-(2-Methoxyphenylthio)thiophene-3-carboxylic acid;
2-(3-Methoxyphenylthio)thiophene-3-carboxylic acid;
2-(4-Methoxyphenylthio)thiophene-3-carboxylic acid;
2-(3-Trifluoromethylphenylthio)thiophene-3-carboxylic acid;
2-(2,5-Dichlorophenylthio)thiophene-3-carboxylic acid;
2-Methylthiothiophene-3-carboxylic acid;
2-Ethylthiothiophene-3-carboxylic acid;
2-Butylthiothiophene-3-carboxylic acid; and
2-Pentylthiothiophene-3-carboxylic acid.

EXAMPLE 33

5-Thioether derivatives of Furan-2-carboxylic Acids

Following the procedure of Manly and Amstutz [J. Org. Chem. 21, 516–19 (1956)], methyl 5-bromofuran-2-carboxylate is reacted with the cationic salts of 2-methylthiophenol, 3-methylthiophenol, 4-methylthiophenyl, 3,5-dimethylthiophenol, 2-isopropylthiophenol, 2-methoxythiophenol, 4-methoxythiophenol, 2-chlorothiophenol, 3-chlorophiophenol, 4-chlorothiophenol, 2,5-dichlorothiophenol, 3,5-dichlorothiophenol, 2-fluorothiophenol, 3-fluorothiophenol, 4-fluorothiophenol, 2,5-difluorothiophenol, 3,5-difluorothiophenol, 2,3,5,6-tetrafluorophenol, 5-fluoro-2-methylthiophenol 3-trifluorothiophenol, 1-thionaphthol or pentyl mercaptan and the esters thereby formed hydrolyzed to yield:

5-(2-Methylphenylthio)furan-2-carboxylic acid;
5-(3-Methylphenylthio)furan-2-carboxylic acid;
5-(4-Methylphenylthio)furan-2-carboxylic acid;
5-(3,5-Dimethylphenylthio)furan-2-carboxylic acid;
5-(2-Isopropylphenylthio)furan-2-carboxylic acid;
5-(2-Methoxyphenylthio)furan-2-carboxylic acid;
5-(4-Methoxyphenylthio)furan-2-carboxylic acid;

5-(2-Chlorophenylthio)furan-2-carboxylic acid;
5-(3-Chlorophenylthio)furan-2-carboxylic acid;
5-(4-Chlorophenylthio)furan-2-carboxylic acid;
5-(2,5-Dichlorophenylthio)furan-2-carboxylic acid;
5-(3,5-Dichlorophenylthio)furan-2-carboxylic acid;
5-(2-Fluorophenylthio)furan-2-carboxylic acid;
5-(3-Fluorophenylthio)furan-2-carboxylic acid;
5-(4-Fluorophenylthio)furan-2-carboxylic acid;
5-(2,5-Difluorophenylthio)furan-2-carboxylic acid;
5-(3,5-Difluorophenylthio)furan-2-carboxylic acid;
5-(2,3,5,6-Tetrafluorophenylthio)furan-2-carboxylic acid;
5-(5-Fluoro-2-Methylphenylthio)furan-2-carboxylic acid;
5-(3-Trifluoromethylphenylthio)furan-2-carboxylic acid;
5-(1-Naphthylthio)furan-2-carboxylic acid; and
5-Pentylthiofuran-2-carboxylic acid.

5-(4-Methylphenylthio)furan-2-carboxylic acid, 5-(4-methoxyphenylthio)furan-2-carboxylic acid and 5-(4-chlorophenylthio)furan-2-carboxylic acid are alternatively prepared by oxidation of the corresponding aldehydes [Kada et al., Collection Czechoslov. Chem. Commun. 41, 2571 (1976)].

EXAMPLE 34

2-Ether Derivatives of Furan-3-Carboxylic Acid

Following the procedure of Manly and Amstutz (loc. cit.) 2-bromofuran-3-carboxylic acid [Gilman and Burtner, J. Am. Chem. Soc. 55, 2903 (1933)] is reacted with methoxide, ethoxide and phenoxide to yield, respectively:

2-Methoxyfuran-3-carboxylic acid;
2-Ethoxyfuran-3-carboxylic acid; and
2-Phenoxyfuran-3-carboxylic acid.

EXAMPLE 35

2- and 5-Benzylfuran-3-carboxylic Acid

Employing the Friedel-Crafts procedure of Elliott et al. [J. Chem. Soc. (C), 2551 (1971)], methyl or ethyl 2-chloromethylfuran-3-carboxylate or methyl or ethyl 2-bromomethylfuran-3-carboxylate [Bisagni and Rivalle, Bull. Soc. Chim. Fr., 519 (1974)] is used to alkylate benzene to produce methyl or ethyl 2-benzylfuran-3-carboxylate. Either ester is hydrolyzed by boiling 3 g. in mixture of 40 ml. of methanol and 40 ml. of 1 N sodium hydroxide for 3 hours on a steam bath. The aqueous residue is diluted with an equal volume of water and extracted with ether. The aqueous phase is acidified with conc. hydrochloric acid and product extracted into ethyl acetate. The ethyl acetate is backwashed with water, dried over anhydrous sodium sulfate and evaporated to dryness to yield 2-benzylfuran-3-carboxylic acid.

The same hydrolysis procedure is employed to convert ethyl 5-benzylthiophene-3-carboxylate (Elliott et al., loc. cit.) to 5-benzylthiophene-3-carboxylic acid.

EXAMPLE 36

Phenylthiomethyl Derivatives

Following the procedure of Example 1, ethyl 5-chloromethyl-3-carboxylate [Divald et al., J. Org. Chem. 41, 2835 (1976)], methyl or ethyl 2-chloromethylfuran-3-carboxylate or methyl or ethyl 2-bromomethylfuran-3-carboxylate [Basigne and Rivalle, Bull. Soc. Chim. Fr. 519 (1974)], ethyl 5-chloromethylthiophene-2-carboxylate [Haworth and Jones, J. Chem. Soc., 667 (1944)], or 5-bromomethylthiophene-2-carboxylate [Gogte et al., Tetrahedron 23, 2443 (1967)], methyl 5-bromomethylthiophene-3-carboxylate [derived from the corresponding acid, Janda et al., Collect. Czech. Chem. Commun. 41, 1541 (1976); Stibor et al., loc. cit. 42, 2167 (1977)], and methyl 2-chloromethylthiophene-3-carboxylate [Tagawa et al., Japan. Kokai 76, 136, 697 (1976); Chem. Abst. 87, 53247p] are reacted with the sodium of thiophenol and hydrolyzed to yield, respectively:

5-Phenylthiomethylfuran-3-carboxylic acid;
2-Phenylthiomethylfuran-3-carboxylic acid;
5-Phenylthiomethylthiophene-2-carboxylic acid;
5-Phenylthiomethylthiophene-3-carboxylic acid; and
2-Phenylthiomethylthiophene-3-carboxylic acid.

EXAMPLE 37

Sodium 5-Phenylthiofuran-3-carboxylate

5-Phenylthiofuran-3-carboxylate is combined with an equivalent of sodium ethoxide in ethyl acetate. Sodium 5-phenylthiofuran-3-carboxylate is isolated by concentration to dryness or by precipitation resulting from addition of a non-solvent (ether or hexane).

Substitution of an equivalent amount of diethanol amine for sodium ethoxide is employed to produce diethanolammonium 5-phenylthio-3-carboxylate.

EXAMPLE 38

Potassium 5-(3-Chlorophenylthio)furan-3-carboxylate 5-(3-Chlorophenylthio)furan-3-carboxylate is dissolved in ethyl acetate. An equivalent of ethanolic potassium hydroxide is added. Potassium 5-(3-chlorophenylthio)furan-3-carboxylate is isolated by concentration to dryness or by precipitation resulting from addition of a non-solvent (ether or heptane).

Substitution of an equivalent of N-methylglucamine (meglumine) for the ethanolic potassium hydroxide is employed to produce N-methylglucammonium 5-(3-chlorophenylthio)furan-3-carboxylate.

EXAMPLE 39

Sodium 5-Phenylthiomethylfuran-2-carboxylate

5-Phenylthiomethylfuran-2-carboxylate is dissolved by warming in acetone. An equivalent of sodium methoxide is added with stirring. Sodium 5-phenylthiomethylfuran-2-carboxylate is isolated by evaporation to dryness or by precipitation resulting from addition of a non-solvent (ether or pentane).

Substitution of a molar equivalent of piperazine for sodium methoxide is employed to produce piperazinium 5-phenylthiomethylfuran-2-carboxylate.

EXAMPLE 40

Magnesium 5-Phenylthiothiophene-2-carboxylate

5-Phenylthiothiophene-2-carboxylate and an equivalent quantity of magnesium oleate are each dissolved in ethanol and the solutions mixed. Magnesium 5-phenylthiothiophene-2-carboxylate is isolated by concentration and/or addition of heptane.

Substitution of an equivalent of calcium palmitate for magnesium oleate in this process is employed to produce calcium 5-phenylthiothiophene-2-carboxylate.

EXAMPLE 41

Salt Formation

Alternatively, the acid products of Examples 1 to 35 are converted to the sodium, potassium, ammonium, calcium, magnesium, aluminum, benzathine, choline diethanolamine, ethylenediamine, meglumine, benethamine, diethylamine, piperazine and tromethamine salts by reaction with an equivalent of the appropriate metal hydroxide, ammonium hydroxide or amine in water or ethanol followed by filtration of the salt if it is insoluble or by evaporation of the solvent if the salt is soluble therein.

EXAMPLE 42

Capsules

A blend is prepared containing the following ingredients in the proportion by weight indicated:

| | |
|---|---|
| Calcium carbonate, U.S.P. | 17.6 |
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |
| Magnesium stearate B | 0.35 |

To this blend is added sufficient sodium 5-phenylthiofuran-3-carboxylate to fill standard size capsules so as to contain 500 mg., 300 mg., 100 mg., 50 mg. or 25 mg. of 5-phenylthiofuran-3-carboxylic acid. The portion of blend to active drug is within the limits of 1–0.1 to 1–2, i.e., 27.8 mg. of sodium salt and 250 mg. of blend in a 25 mg. capsule or 556 mg. of sodium salt and 250 mg. of blend in a 500 mg. capsule as examplary of the extremes.

EXAMPLE 43

Tablets

A tablet base is prepared by blending the following ingredients in the proportion by weight indicated:

| | |
|---|---|
| Sucrose, U.S.P. | 80.3 |
| Tapioca Starch | 13.2 |
| Magnesium Stearate | 6.5 |

Into this tablet base there is blended sufficient sodium 5-phenylthiomethylfuran-3-carboxylate to form tablets containing 50 mg., 100 mg or 250 mg. of 5-phenylthiomethylfuran-3-carboxylic acid. The portion of blend to active drug is within the limits of 1–0.167 to 1—1, i.e., 54.8 mg. of sodium salt and 300 mg. of blend in a 50 mg. tablet or 274 mg. of sodium salt and 250 mg. of blend in a 250 mg. tablet.

EXAMPLE 44

Injectable Preparation

A solution for parenteral, especially intramuscular injection is prepared with the following composition:

| | |
|---|---|
| Magnesium 5-phenylthiothiophene-2-carboxylate | 6.32 g.* |
| Magnesium chloride hexahydrate | 12.36 g. |
| Monoethanolamine | 8.85 g. |
| Propylene glycol | 376.00 g. |
| Water, distilled | 94.00 g. |

*Weight equivalent to 6.04 g. 5-phenylthiothiophene-2-carboxylate.

The resultant solution has a concentration of effective ingredient of 10 mg./ml.

EXAMPLE 45

Injectable Preparation

One hundred grams of sterile 5-methoxyfuran-2-carboxylic acid is blended with 250 g. of sterile sodium ascorbate. The blend is dry filled into vials such that each vial contains 55 mg. of the active ingredient. Immediately before use, 11 ml. of sterile water for injection is added to give a 5 mg./ml. solution suitable for intravenous injection.

PREPARATION 1

5-Benzoyl-2-bromothiophene

2-Bromothiophene (9.7 ml., 0.1 mole), benzoyl chloride (11.6 ml., 0.1 mole) and stannic chloride (11.5 ml., 0.1 mole) were combined in 100 ml. of methylene chloride and stirred at room temperature for 4 hours. The reaction mixture was cooled to room temperature, water (65 ml.) was added and the two phase system stirred for 20 minutes. Ether (165 ml.) was added, the organic phase was separated, back-washed with 20 ml. of 1 N sodium hydroxide and twice with 20 ml. of water, and concentrated to an oil (20.8 g.) which crystallized on standing. The crude was melted by warming with 25 ml. of hexane (two phases formed) and cooled to yield purified crystalline 5-benzoyl-2-bromothiophene (16.5 g., m/e 266/268).

PREPARATION 2

5-Benzoyl-2-cyanothiophene

5-Benzoyl-2-bromothiophene (8 g., 30 mmoles) and cuprous cyanide (3.2 g., 36 mmoles) were combined in 75 ml. of quinoline and refluxed for 3 hours. The reaction mixture was cooled to room temperature and solids removed by filtration with 15 ml. of quinoline and 15 ml. of water wash. The combined filtrate and washings were poured into approximately 300 g. of ice, acidified with conc. hydrochloric acid and product extracted into 300 ml. of ether. The ether extract was back-washed with 150 ml. of water, filtered from insolubles and concentrated to yield solid 5-benzoyl-2-cyanothiophene (5.7 g., m.p. 85°–89° C., m/e 213).

PREPARATION 3

5-Benzoylthiophene-2-carboxylic Acid

5-Benzoyl-2-cyanothiophene (4.5 g.) was refluxed for 3 hours with 150 ml. of 5 N sodium hydroxide and 150 ml. of ethanol. The bulk of the ethanol was removed by evaporation under a stream of nitrogen, and the aqueous residue extracted with 200 ml. of ether. Sodium salt of product crystallized in this process and was recovered by filtration. The sodium salt was dissolved in 400 ml. of water, extracted with 150 ml. of ether and the aqueous phase acidified to yield free acid (3.4 g.). This crude product was chromatographed on approximately 150 ml. of silica gel with ethyl acetate-1/hexane-1/5% acetic acid as eluant. Clean, middle fractions were combined, concentrated to dryness and recrystallized from ethyl acetate/hexane to yield purified 5-benzoylthiophene-2-carboxylic acid (2.2 g., m.p. 174°–176° C., m/e 252).

Analysis: Calcd. for $C_{12}H_8O_3S$: C, 62.07; N, 3.47. Found: C, 62.64; H, 3.72.

PREPARATION 4

Benzenesulfenyl Chloride

Under a nitrogen atmosphere, N-chlorosuccinimide (16.3 g., 0.22 mole) was slurried in 125 ml. of methylene chloride. While stirring at room temperature, benzenethiol (13.2 g., 0.12 mole) was added: 2 ml. initial addition to start reflux and the remainder at a rate to maintain reflux (approx. 10 min.). The clear solution which resulted was then stirred at room temperature for 30 minutes. A small amount of precipitate which formed was removed by filtration. The filtrate, assumed to contain the theoretical quantity of benzenesulfenyl chloride (17.3 g., 0.12 mole), was used immediately and directly in the next step. Alternatively, benzenesulfenyl chloride was isolated by evaporation to an oil prior to its further use, and optionally, taken up, without weight determination, in tetrahydrofuran. In the latter case, the tetrahydrofuran was likewise estimated to contain the theoretical quantity of benzenesulfenyl chloride (17.3 g., 0.12 mole).

By the same procedure, equivalent quantities of 1- and 2-thionaphthols are converted to the corresponding 1- and 2-naphthalenesulfenyl chlorides.

PREPARATION 5 o-Toluenesulfenyl Chloride

N-chlorosuccinimide (5.34 g., 40 mmoles) was slurried in 50 ml. of benzene and cooled in an ice-water bath. o-Toluenethiol (4.96 g., 40 mmoles) in 50 ml. of benzene was added dropwise over 15 minutes. The reaction was warmed to room temperature and stirred for approximately 16 hours. The reaction mixture was filtered and o-toluenesulfenyl chloride (5.53 g.) obtained as an oil by evaporation in vacuo.

PREPARATION 6 p-Toluenesulfenyl Chloride

By the method of Preparation 5, 6.2 g. of p-toluenethiol (6.2 g., 50 mmoles) was reacted with N-chlorosuccinimide (6.67 g., 50 mmoles) in 100 ml. of benzene to yield p-toluenesulfenyl chloride (7.0 g.) as an oil.

By the same method m-toluenethiol [Tarbell and Fukushima, Org. Synthesis 27, 81 (1947)] is converted to m-toluenesulfenyl chloride.

PREPARATION 7 o-Chlorobenzenesulfenyl Chloride

Under nitrogen, N-chlorosuccinimide (5.34 g., 40 mmoles) was slurried in 50 ml. of carbon tetrachloride and the stirred mixture cooled in an ice-water bath. o-Chlorothiophenol (5.76 g., 40 mmoles), dissolved in 25 ml. of carbon tetrachloride, was added dropwise. The ice-water bath was removed and the reaction mixture stirred at room temperature for approximately 16 hours. The reaction was filtered, evaporated to an oil, taken up in hexane, refiltered and reconcentrated to yield o-chlorobenzenesulfenyl chloride (6.8 g., oil).

PREPARATION 8 m-Chlorobenzenesulfenyl Chloride

By the same method as Preparation 7, m-chlorothiophenol (5.76 g., 40 mmoles) was converted to m-chlorobenzenesulfenyl chloride (6.09 g. of oil).

PREPARATION 9 p-Chlorobenzenesulfenyl Chloride

Following the method of Harpp and Mathiaparnam [J. Org. Chem. 37, 1372 (1972)], 14.4 g. of p-chlorothiophenol was converted to 16 g. of p-chlorobenzenesulfenyl chloride (oil).

Alternatively, p-chlorosulfenyl chloride is prepared by the procedure of Preparation 7.

PREPARATION 10 p-Fluorobenzenesulfenyl Chloride

Employing the procedure of Preparation 7, p-fluorothiophenol (5.0 g., 39 mmoles) and N-chlorosuccinimide (5.2 g., 39 mmoles) were reacted to form p-fluorobenzenesulfenyl chloride (4.8 g., oil).

By the same procedure m-fluorothiophenol is converted to m-fluorobenzenesulfenyl chloride.

PREPARATION 11 p-Methoxybenzenesulfenyl Chloride

Following the procedure of King and Abikar [Can. J. Chem. 46, 9 (1968)], 50 ml. of carbon tetrachloride was cooled to 0°–5° C. in an ice-water bath and saturated with gaseous chlorine. This cold solution was titrated dropwise into a cold (0°–5° C.) solution of p-methoxythiophenol (5 g.) in 25 ml. of carbon tetrachloride in sufficient quantity to maintain a deep red color. The reaction was evaporated to an oil. Distillation gave purified p-methoxybenzenesulfenyl chloride (3.59 g., b.p. 107° C./4 mm).

By the same procedure or by the procedure of Preparation 7, o-methoxythiophenol and m-methoxythiophenol are converted, respectively, to o-methoxybenzenesulfenyl chloride and m-methoxybenzenesulfenyl chloride.

PREPARATION 12 m-Trifluoromethylbenzenesulfenyl Chloride

The procedure of Preparation 7 was employed to convert m-trifluorothiophenol (7.12 g., 40 mmoles) to m-trifluorobenzenesulfenyl chloride (6.77 g. of oil).

PREPARATION 13

2,5-Dichlorobenzenesulfenyl Chloride

The procedure of Preparation 7 was repeated, reacting a slurry of N-chlorosuccinimide (3.72 g., 27.9 mmoles) in 50 ml. of carbon tetrachloride with 2,5-dichlorothiophenol (5.0 g., 27.9 mmoles) in 25 ml. of carbon tetrachloride. 2,5-Dichlorobenzenesulfenyl chloride (5.1 g.) was isolated as an oil.

PREPARATION 14

Ethylsulfenyl Chloride

Diethyl disulfide (610 mg., 5 mmoles) was dissolved in 10 ml. of carbon tetrachloride. A solution of chlorine in carbon tetrachloride (3.5 ml. of concentration 100 mg./ml.) was added and the solution stirred for 10 minutes at room temperature. The resulting solution, used directly in subsequent steps, was estimated to contain 10 mmoles of ethylsulfenyl chloride. Alternatively, tetrahydrofuran is substituted for carbon tetrachloride by evaporation to an oil and redissolution in tetrahydrofuran.

PREPARATION 15

Butylsulfenyl Chloride

Under nitrogen, dibutyl disulfide (3.56 g., 20 mmoles) was dissolved in 40 ml. of carbon tetrachloride and the stirred solution cooled in an ice-water bath. A solution of chlorine (1.4 g., 20 mmoles) in 14 ml. of carbon tetrachloride was added dropwise. The bath was removed and the solution stirred for 10 minutes at room temperature. The solution estimated to contain 4.96 g. (40 mmoles) of butylsulfenyl chloride was used directly in subsequent steps. Alternatively, the solution is concentrated to an oil and taken up, without transfer, in tetrahydrofuran, the tetrahydrofuran estimated to contain a like quantity of butylsulfenyl chloride.

By the same process, dipentyl disulfide [Miller et al., J. Am. Chem. Soc. 64, 2323 (1942)], is converted to pentylsulfenyl chloride.

I claim:

1. A method of lowering the blood glucose level in a hyperglycemic mammal which comprises administering a compound of structure

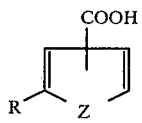

wherein
Z is oxygen or sulfur;
R is (C$_1$-C$_2$)alkoxy;
  phenoxy;
  benzyl;
  phenylthiomethyl;
  phenylthio;
  phenylthio monosubstituted in the 2-, 3- or 4-position with (C$_1$-C$_3$)alkyl, phenyl, methoxy, chloro, fluoro or trifluoromethyl;
  phenylthio disubstituted in the 2,5- or 3,5-positions with methyl, methoxy, chloro, or fluoro;
  2,3,5,6-tetrafluorophenylthio;
  1- or 2-naphthylthio;
  (C$_2$-C$_6$)alkylthio; or
  halo (bromo or chloro); or
a pharmaceutically-acceptable salt thereof, to said hyperglycemic mammal in an amount sufficient to lower said blood glucose level.

2. A method of claim 1 wherein the compound is of structure

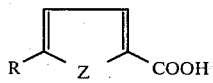

3. A method of claim 2 wherein Z is oxygen.
4. A method of claim 3 wherein R is methoxy, benzyl, phenylthiomethyl, or phenylthio.
5. A method of claim 4 wherein R is methoxy.
6. A method of claim 4 wherein R is benzyl.
7. A method of claim 4 wherein R is phenylthiomethyl.

8. A method of claim 4 wherein R is phenylthio.
9. A method of claim 2 wherein Z is sulfur.
10. A method of claim 9 wherein R is benzyl, phenylthio, 3-methylphenylthio or 3-chlorophenylthio.
11. A method of claim 1 wherein the compound is of structure

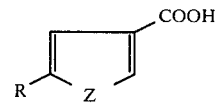

12. A method of claim 11 wherein Z is oxygen.
13. A method of claim 12 wherein R is phenylthio; 3- or 4-methylphenylthio; 2-, 3- or 4-chlorophenylthio; 2-, 3- or 4-fluorophenylthio; 2,5- or 3,5-difluorophenylthio; 2,3,5,6-tetrafluorophenylthio; 3-trifluoromethylphenylthio; or 2-naphthylthio.
14. A method of claim 13 wherein R is phenylthio.
15. A method of claim 13 wherein R is 3-chlorophenylthio.
16. A method of claim 13 wherein R is 2-fluorophenylthio.
17. A method of claim 13 wherein R is 3-fluorophenylthio.
18. A method of claim 11 wherein Z is sulfur.
19. A method of claim 18 wherein R is phenylthio.
20. A method of claim 1 wherein the compound is of structure

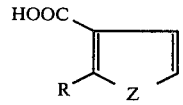

21. A method of claim 20 wherein Z is oxygen.
22. A method of claim 21 wherein R is phenylthio.
23. A method of claim 20 wherein Z is sulfur.
24. A method of claim 23 wherein R is phenylthio.
25. A pharmaceutical composition suitable for oral or parenteral administration which comprises an amount sufficient to lower the blood glucose level in a hyperglycemic animal of a compound of the structure

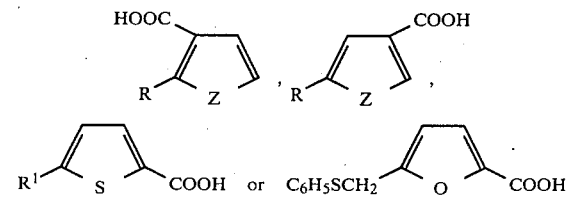

wherein
Z is oxygen or sulfur;
R is (C$_1$-C$_2$)alkoxy;
  phenoxy;
  phenylthiomethyl;
  phenylthio;
  phenylthio monosubstituted in the 2-, 3- or 4-position with (C$_1$-C$_3$)alkyl, phenyl, methoxy, chloro, fluoro or trifluoromethyl;
  phenylthio disubstituted in the 2,5- or 3,5-positions with methyl, methoxy, chloro, or fluoro;
  2,3,5,6-tetrafluorophenylthio;
  1- or 2-naphthylthio; or
  (C$_2$-C$_6$)alkylthio; and R¹ is phenoxy;
phenylthiomethyl;
phenylthio;
phenylthio monosubstituted in the 2-, 3- or 4-position with (C₁–C₃)alkyl, phenyl, methoxy, chloro, fluoro or trifluoromethyl;
phenylthio disubstituted in the 2,5- or 3,5-positions with methyl, methoxy, chloro, or fluoro;
2,3,5,6-tetrafluorophenylthio;
1- or 2-naphthylthio; or
(C₂–C₆)alkylthio; or
a pharmaceutically-acceptable salt thereof, together with a pharmaceutically acceptable carrier or diluent.

26. A pharmaceutical composition of claim 25 wherein the compound is of the structure

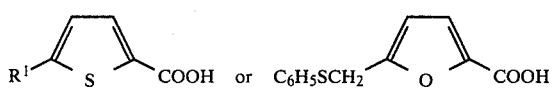

27. A pharmaceutical composition of claim 26 wherein the compound is of the structure

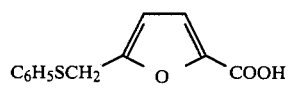

28. A pharmaceutical composition of claim 26 wherein the compound is of the structure

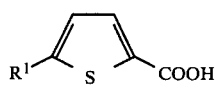

29. A pharmaceutical composition of claim 28 wherein R¹ is phenylthio, 3-methylphenylthio or 3-chlorophenylthio.

30. A pharmaceutical composition of claim 25 wherein the compound is of the structure

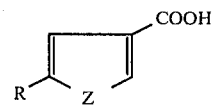

31. A pharmaceutical composition of claim 30 wherein Z is oxygen.

32. A pharmaceutical composition of claim 31 wherein R is phenylthio; 3- or 4-methylphenylthio; 2-, 3- or 4-chlorophenylthio; 2-, 3- or 4-fluorophenylthio; 2,5- or 3,5-difluorophenylthio; 2,3,5,6-tetrafluorophenylthio; 3-trifluoromethylphenylthio; or 2-naphthylthio.

33. A pharmaceutical composition of claim 32 wherein R is phenylthio.

34. A pharmaceutical composition of claim 32 wherein R is 3-chlorophenylthio.

35. A pharmaceutical composition of claim 32 wherein R is 2-fluorophenylthio.

36. A pharmaceutical composition of claim 32 wherein R is 3-fluorophenylthio.

37. A pharmaceutical composition of claim 30 wherein Z is sulfur.

38. A pharmaceutical composition of claim 37 wherein R is phenylthio.

39. A pharmaceutical composition of claim 25 wherein the compound is of the structure

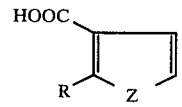

40. A pharmaceutical composition of claim 39 wherein Z is oxygen.

41. A pharmaceutical composition of claim 40 wherein R is phenylthio.

42. A pharmaceutical composition of claim 39 wherein Z is sulfur.

43. A pharmaceutical composition of claim 42 wherein R is phenylthio.

* * * * *

UNITED STATES PATENT OFFICE
CERTIFICATE OF CORRECTION

Patent No. 4,282,246    Dated August 4, 1981

Inventor(s) Gerald F. Holland

It is certified that error appears in the above-identified patent and that said Letters Patent are hereby corrected as shown below:

In the title page, item [54] should read "ANTIDIABETIC FURANCARBOXYLIC AND THIOPHENECARBOXYLIC ACIDS".

Column 1, lines 1-3, the title should read "ANTIDIABETIC FURANCARBOXYLIC AND THIOPHENECARBOXYLIC ACIDS".

Column 2, line 46, "compound" should read --compounds--.

Column 16, line 59, "$f_2$" should read --$F_2$--.

Signed and Sealed this

Twenty-fourth Day of November 1981

[SEAL]

Attest:

Attesting Officer

GERALD J. MOSSINGHOFF

Commissioner of Patents and Trademarks